May 11, 1954 H. C. SWIM Plant Pat. 1,277
ROSE PLANT
Filed March 24, 1953
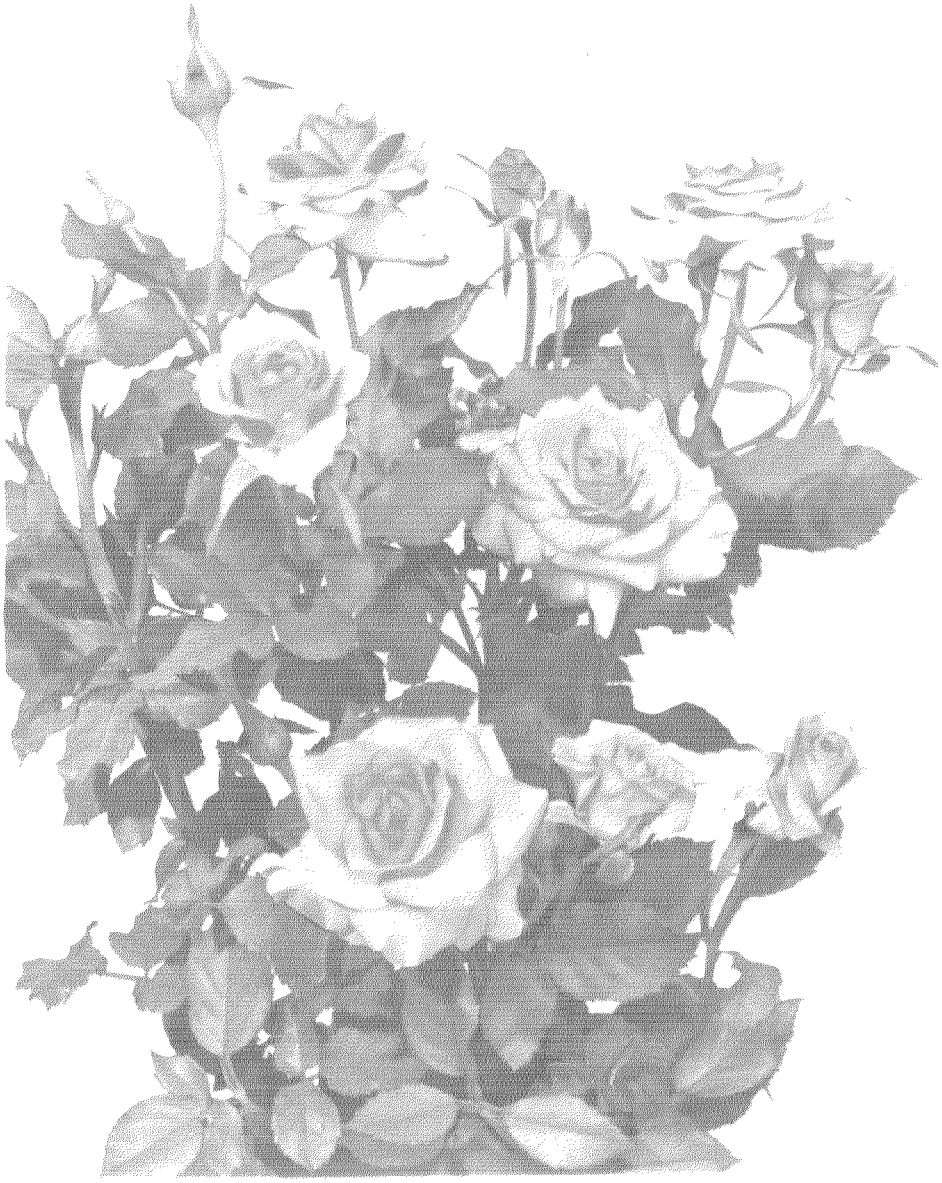
Inventor.
H. C. Swim
By: Robb & Robb
Attorneys.

Patented May 11, 1954

Plant Pat. 1,277

UNITED STATES PATENT OFFICE 1,277

ROSE PLANT

Herbert C. Swim, Ontario, Calif., assignor to Armstrong Nurseries, Inc., Ontario, Calif., a corporation of California Application March 24, 1953, Serial No. 344,484

1 Claim. ( Cl. 47—61)

The present invention relates to a new and distinct variety of rose plant of the hybrid polyantha class, which was originated by me by crossing the variety "Minna Kordes," known in the United States as "World's Fair" (Plant Patent No. 362) with the variety "Pinocchio" (Plant Patent No. 484).

The primary objective in making this cross was to produce a new variety of rose plant which combines the best characteristics of the two parent varieties aforesaid, and thereby is characterized by a new and unique combination of features heretofore unknown in varieties of this class. The outstanding features of this new variety which contribute to the novelty and distinctiveness thereof are as follows:

(1) The many-flowered cluster habit of growth comparable to that of the pollen parent "Pinocchio";

(2) The relatively large flower size which is inherited from the seed parent "World's Fair";

(3) The deep pink general color tonality of the flowers which is definitely different from the color of the flowers of both parents, as well as from all other varieties of its class;

(4) The moderate fragrance of the flowers, as derived from both parents;

(5) The presence of few prickles on the flowering stems and few prickles on the entire plant, the number of prickles being considerably fewer than are found on the flowering stems and plants of either parent; and (6) The abundant foliage which is characteristic of "World's Fair."

In comparison with its seed parent, "World's Fair," the blooms of my new variety are deep pink in color, whereas those of this parent are deep red or deep crimson, usually fading to scarlet; there are fewer prickles on the flowering stems and on the entire plant than are present in the variety "World's Fair"; the blooms of my new variety are produced in many-flowered clusters, with substantially more flowers per cluster than those of "World's Fair"; and the blooms have more petals than do those of this parent, usually numbering from 20 to 28 petals per flower as compared with 18 to 20 petals of "World's Fair."

As compared with its pollen parent "Pinocchio," the color of the blooms of my new variety is deep pink, whereas that of the blooms of "Pinocchio" is best described as pink-suffused salmon; there are fewer prickles on the stems and canes of my new variety than are found on the plants of this parent; the foliage of my new variety is produced in greater abundance than is that of this parent;

and the blooms of my new variety are substantially larger in size than those of this parent.

Asexual reproduction of my new variety by budding at Ontario, California, shows that the foregoing characteristics and distinctions come true to form and are established and transmitted through succeeding propagations.

The accompanying drawing shows specimens of the flowers, foliage and stems of my new variety in different stages of development.

The following is a detailed description of my new variety, with color terminology in accordance with Robert F. Wilson's Horticultural Colour Chart (hereinafter abbreviated as "Wilson") and in accordance with Ridgway's Color Standards and Nomenclature (hereinafter abbreviated as "Ridgway"):

Type: Bush; outdoor; seedling; for cut flowers and for garden decoration.

Class: Hybrid polyantha.

Breeding: Seedling.

*Seed parent.*—"Minna Kordes" or "World's Fair" as known in the United States.

*Pollen parent.*—"Pinocchio."

Propagation: Holds its distinguishing characteristics through succeeding propagations by budding.

*Flower*

Locality where grown and observed: Ontario, California.

Flowers borne: Usually 4 or 5 or more to stem; in regular, flat to somewhat rounded clusters; on strong, long stems.

Quantity of bloom: Abundant, outdoors.

Continuity: Continuous during growing season.

Fragrance: Moderate; musk to tea.

Bud:

*Peduncle.*—Sometimes short, but usually average length; average caliper; erect; smooth; numerous gland - tipped cilia. Color—near Lettuce Green, Plate V (Ridgway).

*Before calyx breaks.* — Size — medium. Form—medium length; ovoid; with foliaceous appendages and few gland-tipped cilia on the surface of the bud; usually with fairly stout, much-cut foliaceous parts extending beyond the tip of the bud equal to ¼ to ½ of its length.

*As calyx breaks.*—Color—between Neyron Rose, Plate 623, page 76 (Wilson) and Neyron Rose, Plate 623/1, page 76 (Wilson).

*Sepals.*—Inner surface with fine, woolly tomentum; margins: Alternate sepals with fine, woolly tomentum; others lined with stipitate glands.

*As first petal opens.* — Size — Average. Form — medium length; urn-shaped. Color: outside—between Neyron Rose, Plate 623/1, page 76 (Wilson) and Neyron Rose, Plate 623/2, page 76 (Wilson); small area at base of petal near attachment near Sulphur Yellow, Plate 1/3, page 1 (Wilson); inside—near Neyron Rose, Plate 623/1, page 76 (Wilson); small area at base of petal near attachment near Sulphur Yellow, Plate 1/3, page 1 (Wilson).

*Opening.*—Opens up well; is not retarded from opening by cold, hot, wet or dry weather.

Bloom:

*Size (when fully open).*—Average too large for its class; 2½ inches to 3 inches.

*Petalage.*—Double; from 20 to 28 petals, plus 6 to 11 petaloids; arranged regularly.

*Form.*—High-centered at first; becoming open later; petals being at first cupped, usually with lateral margins only slightly reflexed for upper ⅓ of petal, and apex sometimes reflexed slightly; outermost petals with lateral margins reflexed from ½ to ¾ of upper portion of petal, and apex sometimes reflexed; becoming flat later at maturity, with lateral margins reflexed from ½ to ¾ of upper part of petal and apex sometimes reflexed ⅓ to ½ of petal length.

Petals:

*Texture.*—Medium thickness; leathery; with inside somewhat velvety and outside satiny.

*Shape.*—Outside—broadly obovate, with apex somewhat flat. Intermediate — obovate, with apex rounded to somewhat flat. Inside—obovate, but sometimes somewhat irregular, with apex rounded and rarely with 1 or 2 notches.

This description of a newly opened flower was made from a rose grown outdoors in the month of October, at Ontario, California:

*Color.*—Outside petal: outside surface—between Neyron Rose, Plate 623/1, page 76 (Wilson) and Neyron Rose, Plate 623/2, page 76 (Wilson); small area at base of petal near attachment near Sulphur Yellow, Plate 1/3, page 1 (Wilson); inside surface—near Neyron Rose, Plate 623/1, page 76 (Wilson); small area at base of petal near attachment near Sulphur Yellow, Plate 1/3, page 1 (Wilson). Intermediate petal: outside surface—between Neyron Rose, Plate 623/1, page 76 (Wilson) and Neyron Rose, Plate 623/2, page 76 (Wilson); small area at base of petal near attachment near Sulphur Yellow, Plate 1/3, page 1 (Wilson); inside surface—between Neyron Rose, Plate 623, page 76 (Wilson) and Neyron Rose, Plate 623/1, page 76 (Wilson); small area at base of petal near attachment near Sulphur Yellow, Plate 1/3, page 1 (Wilson). Inner petal: outside surface—between Neyron Rose, Plate 623, page 76 (Wilson) and Neyron Rose, Plate 623/1, page 76 (Wilson); small area at base of petal near attachment near Sulphur Yellow, Plate 1/3, page 1 (Wilson); inside surface—between Neyron Rose, Plate 623, page 76 (Wilson) and Neyron Rose, Plate 623/1, page 76 (Wilson); small area at base of petal near attachment near Sulphur Yellow, Plate 1/3, page 1 (Wilson).

This description was made from a rose that was open for three days outdoors in the month of October, at Ontario, California:

*Color.*—Outside petal: outside surface—near Phlox Pink, Plate 625/3, page 77 (Wilson); small area at base of petal near attachment near Sulphur Yellow, Plate 1/3, page 1 (Wilson); inside surface—between Phlox Pink, Plate 625/2, page 77 (Wilson) and Phlox Pink, Plate 625/3, page 77 (Wilson); small area at base of petal near attachment near Sulphur Yellow, Plate 1/3, page 1 (Wilson). Inside petal: outside surface—between Phlox Pink, Plate 625/2, page 77 (Wilson) and Phlox Pink, Plate 625/3, page 77 (Wilson); small area at base of petal near attachment near Sulphur Yellow, Plate 1/3, page 1 (Wilson); inside surface—near Phlox Pink, Plate 625/2, page 77 (Wilson); small area at base of petal near attachment near Sulphur Yellow, Plate 1/3, page 1 (Wilson).

*General color effect.*—Newly opened flower—between Neyron Rose, Plate 623, page 76 (Wilson) and Neyron Rose, Plate 623/1, page 76 (Wilson). 3-days open—between Phlox Pink, Plate 625/2, page 77 (Wilson) and Phlox Pink, Plate 625/3, page 77 (Wilson); small area at base of petal near attachment near Sulphur Yellow, Plate 1/3, page 1 (Wilson).

*Behavior.*—Drop off cleanly; not particularly affected by hot, cold, wet or dry weather.

*Flower longevity.*—On bush in garden—3 to 4 days in October. Cut roses grown outdoors and kept at living-room temperatures—4 to 5 days in October.

*Reproductive organs*

Stamens: Average to many; arranged regularly about pistils.

Filaments: Short to medium length; 4 to 8 mm. in length; most with anthers. Color—near Sulphur Yellow, Plate 1/2, page 1 (Wilson).

Anthers: Medium size; all open approximately at once. Color: upper side—margin between Lemon Yellow, Plate 4/2, page 4 (Wilson) and Buttercup Yellow, Plate 5/2, page 5 (Wilson); remainder near Canary Yellow, Plate 2/3, page 2 Wilson); under side—margin between Lemon Yellow, Plate 4/2, page 4 (Wilson) and Buttercup Yellow, Plate 5/2, page 5 (Wilson); remainder near Canary Yellow, Plate 2/3, page 2 (Wilson).

Pollen: Moderate to abundant. Color—near Indian Yellow, Plate 6/2, page 6 (Wilson).

Pistils: Average number; approximately 60 in number.

Styles: Moderately even; average length; somewhat loosely bunched; 5 to 9 mm. in length. Color—upper ⅓ near Carmine, Plate 21/1, page 21 (Wilson); remainder near Sap Green, Plate 62/1, page 62 (Wilson).

Stigma: Color—between Aureolin, Plate 3/3, page 3 (Wilson) and Lemon Yellow, Plate 4/3, page 4 (Wilson).

Ovaries: Most enclosed in, but some protruding from calyx.

Hips: Average length to long; pear-shaped; smooth; walls moderately thick and fleshy. Color (⅔ mature)—between Javel Green, Plate V (Ridgway) and Oil Green, Plate V (Ridgway).

Sepals: Permanent; medium length; some curled and some recurved. Color: inside—between Courge Green, Plate XVII (Ridgway) and Biscay Green, Plate XVII (Ridgway), masked with white woolly tomentum; outside—between Courge Green, Plate XVII (Ridgway) and Biscay Green, Plate XVII (Ridgway).

Seeds: Few, medium size; 8 to 12 in number.

*Plant*

Foliage:

*Leaves.*—Compound of usually 5 to 7 leaflets; abundant; medium size; leathery; semi-glossy.

*Leaflets.*—Shape—ovoid, with acute apex and round base. Margin—doubly serrate.

*Color.*—Mature: upper surface—near Forest Green, Plate XVII (Ridgway); under surface—between Turtle Green, Plate XXXII (Ridgway) and Chromium Green, Plate XXXII (Ridgway). Young: upper surface—near Bice Green, Plate XVII (Ridgway), shaded with near Dark Perilla Purple, Plate XXXVII (Ridgway); under surface—near Light Bice Green, Plate XVII (Ridgway), shaded with near Corinthian Purple, Plate XXXVIII (Ridgway).

*Rachis (the supporting stem of the compound leaf).*—Average size. Upper side—grooved, with few hairs and some stipitate glands on edges. Under side—very few prickles; with some stipitate glands.

*Stipules.*—Medium length; medium width; short to medium length points usually turning out at an angle of more than 45°.

*Disease.*—Average resistance to mildew, as compared with other varieties grown under comparable cultural conditions at Ontario, California.

Growth:

*Habit.*—Bushy; upright; much-branched.

*Growth.*—Very vigorous.

*Canes.*—Medium caliper in relation to length.

*Main stems.*—Color—between Yellowish Oil Green, Plate V (Ridgway) and Oil Green, Plate V (Ridgway). Large prickles—very few; medium length; hooked slightly downward; with medium length, narrow to somewhat rounded base; color—between Mikado Brown, Plate XXIX (Ridgway) and Sayal Brown, Plate XXIX (Ridgway). Small prickles—none to very few; Color—near Sayal Brown, Plate XXIX (Ridgway). Hairs—None.

*Branches.*—Color—Between Oil Green, Plate V (Ridgway) and Lettuce Green, Plate V (Ridgway). Large prickles—very few; medium length; hooked slightly downward; with medium length, narrow to somewhat rounded base; color—between Sayal Brown, Plate XXIX (Ridgway) and Tawny-Olive, Plate XXIX (Ridgway). Small prickles—none to very few; color—between Sayal Brown, Plate XXIX (Ridgway) and Tawny-Olive, Plate XXIX (Ridgway). Hairs—none.

*New Shoots.*—Color—between Lettuce Green. Plate V (Ridgway) and Parrot Green, Plate VI (Ridgway), shaded very slightly with near Ocher Red, Plate XXVII (Ridgway). Large prickles—none to very few; medium length; hooked slightly downward; with medium length, narrow to somewhat rounded base; Color—near Light Dull Green-Yellow, Plate XVII (Ridgway), very heavily shaded with near Corinthian Purple, Plate XXXVIII (Ridgway). Small prickles—none to few; color—near Light Dull Green-Yellow, Plate XVII (Ridgway), very heavily shaded with near Corinthian Purple, Plate XXXVII (Ridgway). Hairs—none.

I claim:

A new and distinct variety of rose plant of the hybrid polyantha class, substantially as herein shown and described, characterized particularly as to novelty by its abundant foliage, by its many-flowered cluster habit of growth, by the relatively large size and moderate fragrance of its flowers, by the deep pink general color tonality of its flowers, and by the relatively few prickles on the flowering stems and on the entire plant.

No references cited.